United States Patent [19]
Finn et al.

[11] Patent Number: 5,474,551
[45] Date of Patent: Dec. 12, 1995

[54] UNIVERSAL COUPLER FOR SPINAL FIXATION

[75] Inventors: Charles A. Finn, Tierra Verde, Fla.; Scott Sherman, Horn Lake, Miss.

[73] Assignee: Smith & Nephew Richards, Inc., Memphis, Tenn.

[21] Appl. No.: 342,226

[22] Filed: Nov. 18, 1994

[51] Int. Cl.⁶ .......................... A61B 17/70; A61B 17/86
[52] U.S. Cl. ................................... 606/61; 606/73
[58] Field of Search ................... 606/61, 60, 69, 606/70, 71, 73

[56] References Cited

U.S. PATENT DOCUMENTS

| | | |
|---|---|---|
| 4,569,338 | 2/1986 | Edwards . |
| 4,648,388 | 3/1987 | Steffee . |
| 4,771,767 | 9/1988 | Steffee . |
| 5,024,213 | 6/1991 | Asher et al. . |
| 5,053,034 | 10/1991 | Olerud . |
| 5,129,900 | 7/1992 | Asher et al. . |
| 5,176,679 | 1/1993 | Lin . |
| 5,306,275 | 4/1994 | Bryan . |
| 5,344,422 | 9/1994 | Frigg . |
| 5,437,669 | 8/1995 | Yuan et al. ................................ 606/61 |

FOREIGN PATENT DOCUMENTS

9423661 10/1994 WIPO ........................ 606/61

Primary Examiner—Stephen C. Pellegrino
Assistant Examiner—Scott B. Markow
Attorney, Agent, or Firm—Pravel, Hewitt, Kimball & Krieger

[57] ABSTRACT

A spinal rod coupler assembly providing four degrees of freedom for connecting a spinal rod to a vertebrae of a patient which includes a tubular coupler member, an eyebolt, an insert and a set screw. The coupler member has a longitudinal bore, a central axis, and an end portion that is open ended and internally threaded and a second end portion that is closed. A plurality of openings in the tubular coupler member that includes a first pair of openings intersecting the central axis of the bore at generally right angles and a second pair of openings intersecting the central axis of the bore at generally right angles. The first and second pairs of openings being perpendicular to each other. The first pair of openings are sized and shaped to receive a spinal rod. The eyebolt has a shank portion and an eye portion, with the shank portion being insertable through the second pair of openings of the coupler body. The eye portion has an opening sized and shaped to mate with a selected bone bolt or bone screw. The insert fits within the bore and has opposed, arc-shaped end portions with recesses for engaging the spinal rod and eyebolt member. The set screw threadably engages the internally threaded end portion of the bore and tightens the assembly of the rod, insert, and eyebolt within the coupler member.

16 Claims, 6 Drawing Sheets

UNIVERSAL COUPLER FOR SPINAL FIXATION

FIELD OF THE INVENTION

The present invention relates to spinal fixation devices, and more particularly, relates to an improved spinal fixation connector that allows for adjustment in four axes of movement when attaching a longitudinal rod to a vertebrae of a spinal column.

BACKGROUND OF THE INVENTION

There are a number of surgical procedures that require a fixation of portions of the spine with respect to one another. Typically, bone screws or bolts are employed in the fixation of the spine wherein the bone screws or bolts are implanted in a surgical procedure involving the formation of one or more surgical openings in adjacent portions of the spine, for implanting the threaded bone bolts or screws into the vertebrae. Structures such as longitudinal rods or plates extend between the various spine members and are connected to the implanted bone bolts or screws with connector devices.

Connectors for attaching the rods or plates to vertebrae of a spinal column are known in the art. However, current bolt to rod connectors do not allow for adjustability in multiple planes in order to better conform to the anatomical structure of the patient and to eliminate initial stresses on the spinal fixation construct. In spinal surgery that requires distraction, compression, and rotation of the construct to obtain proper assembly, stresses are put on the component parts of existing spinal fixation systems and on the vertebral column, which are not designed to accommodate stresses much higher than those encountered during normal patient activity. By reducing the initial stresses on the construct and the vertebral column, the connector of the present invention allows the entire strength of the connector to be reserved for stresses encountered during patient activity. This provides a spinal construct for a non-compliant patient with activity limitations that is less likely to fail than one with initial high stresses.

Additionally, some existing fixation systems, such as U.S. Pat. Nos. 5,209,752 and 5,176,697, require lateral or medial approaches to assemble and tighten the construct which causes complicated surgical procedures due to the soft tissues that are lateral to the incision. Potential damage can also occur to neurological elements that are medial to the construct.

Current spinal fixation systems, for example such as those shown in U.S. Pat. Nos. 4,719,905 and 5,296,014, also have many pieces to assemble and lack anatomical adjustability which results in long surgeries that put increased stresses on the surgeon and surgical staff. Long surgical times increases patient morbidity due to blood loss and stresses of anesthesia. The large number of pieces in current fixation systems require hospitals to keep large inventories which is difficult during the present time of medical cost containment.

Accordingly, it is a principal object of the present invention to provide a simple and fast way to attach a spinal rod to the spine. The "single piece" (4 pieces pre-assembled) connector of the present invention facilitates rapid assembly during implantation of the fixation construct. This reduces operating time, blood loss and complications which makes the present invention more appealing to surgeons who will spend less time assembling and adjusting spinal fixation constructs in the operating room.

It is another object of the present invention to provide a spinal fixation connector that has a wide range of adjustability to accommodate a range of anatomical variations and to eliminate the initial stresses on the spinal fixation construct.

It is a further object of the present invention to provide a connector that is secured by means of a single set screw that is accessed from a posterior approach. This provides fewer screws for the surgeon to tighten and makes the securing and tightening of the spinal construct easier to access.

It is a further object of the present invention to provide a connector that allows adjustment in four axes of movement that includes a cephalad/caudal direction, a medial/lateral direction and angulation in a sagittal plane and a transverse plane when the assembly is being implanted in a patient.

SUMMARY OF THE INVENTION

The present invention provides a coupler assembly having four axes of movement for connecting a spinal rod to a vertebrae of a patient with a bone bolt or bone screw. The coupler assembly includes a tubular coupler member having a longitudinal bore surrounded by a wall. The bore has a central axis and first and second end portions with one end being open and internally threaded and the other end portion being closed. A plurality of openings are formed through the wall of the tubular coupler member with each of the openings communicating with the bore.

The plurality of openings include a first pair of openings aligned along a first line that intersects the central axis of the bore at generally right angles, and a second pair of openings aligned along a second line that intersects the central axis of the bore at generally right angles. The first and second pairs of openings are generally perpendicular to each other and are spaced apart so that the periphery of the first pair of openings is spaced longitudinally from the periphery of the second pair of openings. The first pair of openings is sized and shaped to receive a spinal rod with the spinal rod's longitudinal axis aligning with the first line of the first pair of openings of the coupler body.

The coupler assembly also includes an eyebolt having a shank portion with a central axis and an eye portion. The shank portion is insertable through the second pair of openings of the coupler body, with the central axis of the shank aligning with the second line of the second pair of openings. The eye portion of the eyebolt has an opening sized and shaped to mate with a selected bone bolt or bone screw.

An insert having an outer surface that generally conforms to the shape of the bore, fits within the bore. The insert has opposed, arc-shaped end portions with recesses for engaging the spinal rod on one end and the eyebolt on the other end. A set screw threadably engages the internally threaded end portion of the bore so that the set screw tightens the assembly of the rod, insert, and eyebolt within the coupler member when tightened down.

The coupler assembly of the present invention provides for movement along four axes that includes a cephalad/caudad direction, a medial/lateral direction, a sagittal plane and transverse plane when the assembly is being implanted in a patient.

BRIEF DESCRIPTION OF THE DRAWINGS

A better understanding of the invention can be obtained when the detailed description of exemplary embodiments set forth below is reviewed in conjunction with the accompanying drawings, in which:

FIG. 8A is a side perspective view of the eyebolt of the present invention;

FIG. 8B is an end plan view taken along sight line 8B—8B in FIG. 8a;

DETAILED DESCRIPTION OF PREFERRED EMBODIMENT

Figure 1:
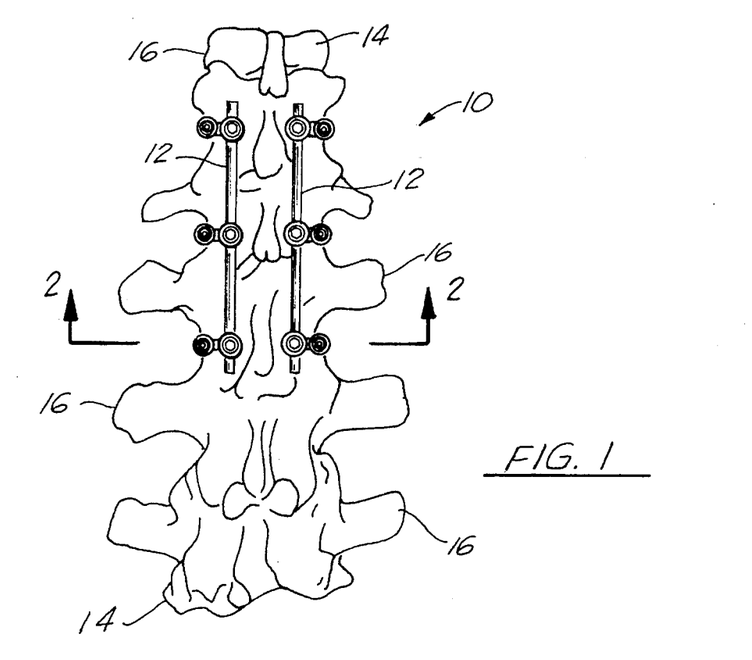
FIG. 1 is a posterior view of a portion of a vertebral column, showing a spinal fixation device connected to the vertebrae by connectors embodying the present invention.
Figure 2:
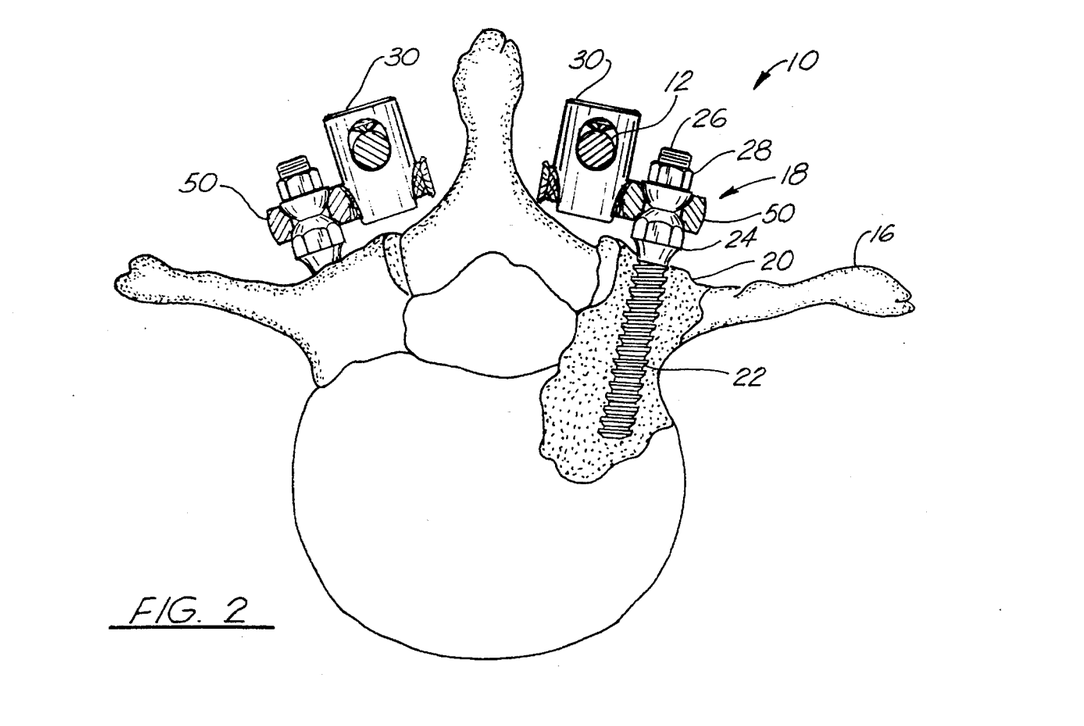
FIG. 2 is a partial cross-sectional view taken along sight line 2—2 in FIG. 1, illustrating the manor in which the apparatus of the present invention connect the spinal rods to a vertebrae.

FIGS. 1 and 2 show the preferred embodiment of the coupler assembly of the present invention, designated generally by the numeral 10 implanted in a spinal column. Coupler assembly 10 includes a coupler body or member 30, an eyebolt member 50, an insert 70 and a set screw 80, and is used to attach longitudinal rods 12 to a vertebral column 14 comprising a plurality of vertebrae 16. The coupler assembly 10 is shown attached to three vertebrae 16 as part of a spinal implant system that is used to hold and stabilize vertebrae 16. Although the attachment of only three vertebrae 16 is shown, it should be understood that the number of assemblies 10 used can vary such that any number of vertebrae can be held in place.

Figure 3:
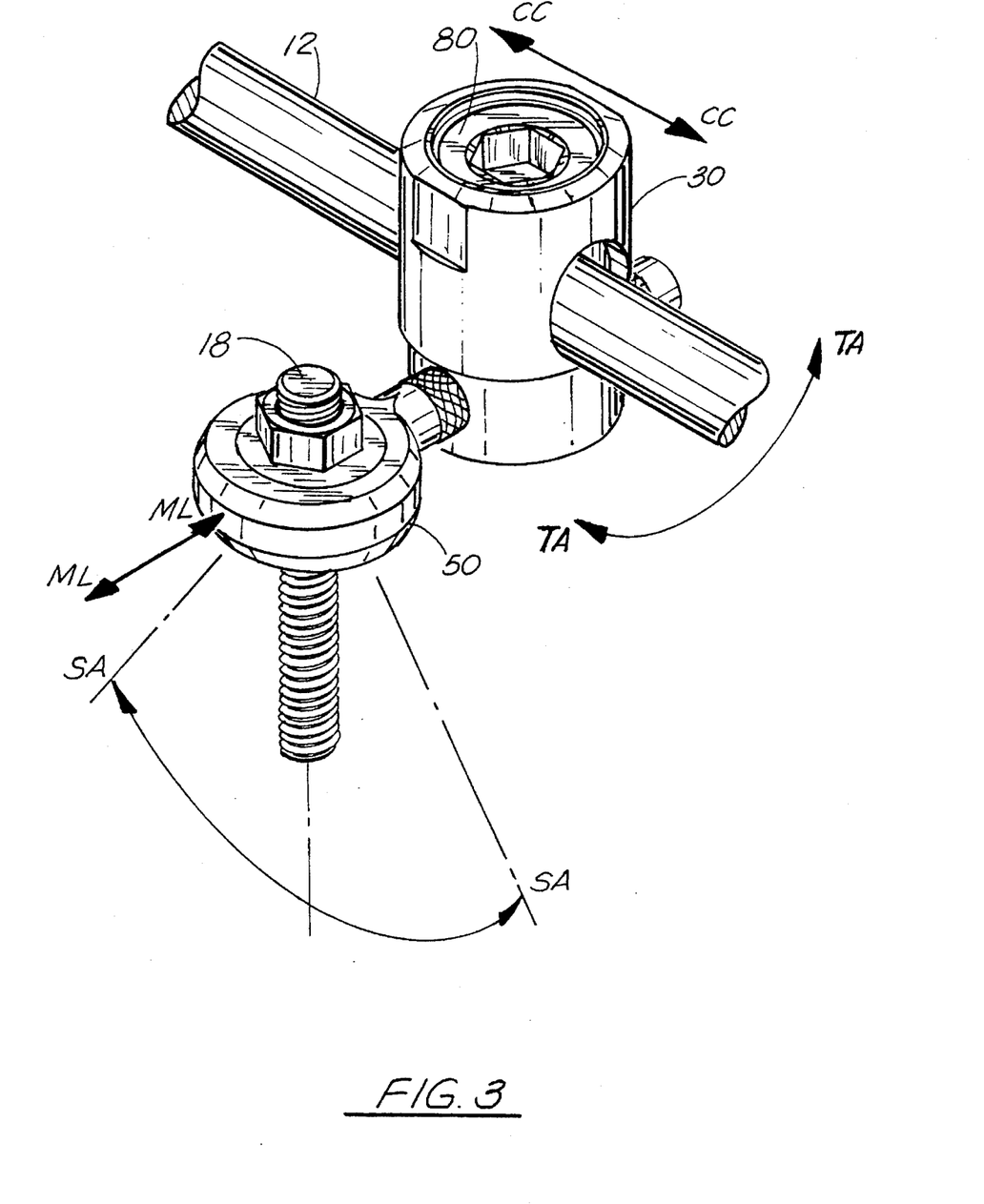
FIG. 3 is a perspective view of the preferred embodiment of the apparatus of the present invention with a spinal rod and bone screw inserted in the apparatus.
Figures 4, 4A:
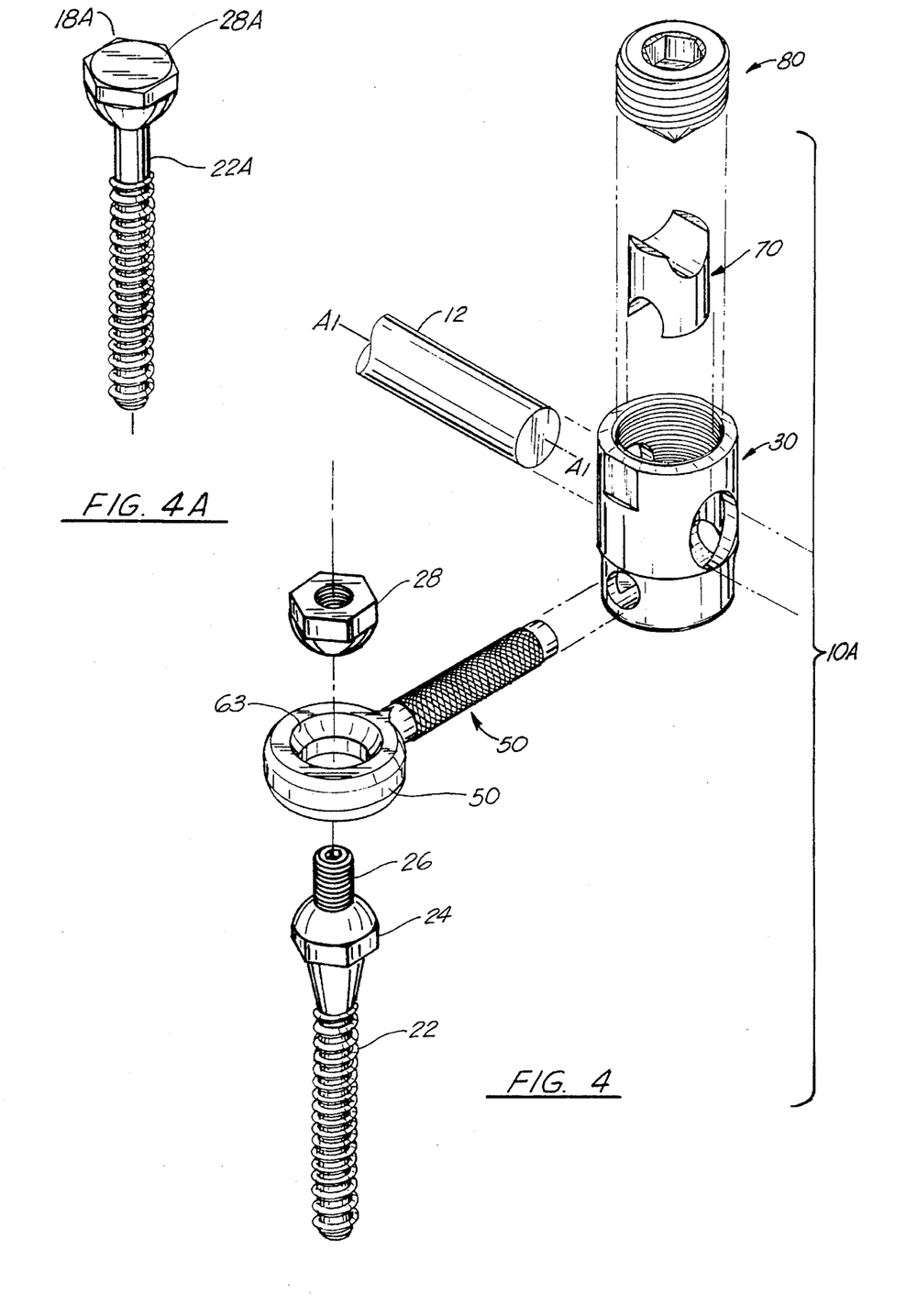
FIG. 4 is an exploded perspective view of the preferred embodiment of the apparatus of the present invention.
FIG. 4A is a side plan view of an alternate bone fastener.

Each of the assemblies 10 is connected to a respective vertebrae 16 by a fastener 18 which may be either a bone bolt (FIGS. 2, 3, 4) or a bone screw 18A (FIG. 4A). The fastener 18 is shown in FIGS. 2, 3 and 4 as bone bolt 18 having a first threaded end portion 22 for threaded engagement with an opening formed in a pedicle 20 of the vertebrae 16. Bolt 18 includes a shoulder portion 24 which establishes how far the first threaded end portion 22 can extend into the vertebrae 16 and spaces the assembly 10 away from the vertebrae 16. Bolt 18 has a second threaded end portion 26 extending past the pedicle 20 for engaging the eyebolt 50 of the assembly 10. The bone bolt 18 also includes a nut 28 that can be threaded upon the threaded end portion 26 of the bolt 18 to secure eyebolt 50 of assembly 10 against the bolt shoulder 24. Bone screw 18A includes a first threaded end portion 22A and a head portion 28A having a spherically shaped lower portion.

After bone bolt 18 has been implanted in pedicle 20 of the vertebrae 16, assembly 10 is placed over the threaded end portion of 26 of the bolt 18. The nut 28 is threaded over the end portion 26 in order to securely fasten the bone bolt 18 to the assembly 10. The longitudinal rod 12, having a longitudinal axis A1—A1 (FIG. 4) is placed through an opening in the assembly 10 and the set screw 80 secures the entire assembly 10A together (FIGS. 3, 4). The coupler assembly 10A includes the coupler assembly 10, the spinal rod 12 and the bone fastener 18.

In the embodiment of the present invention shown in FIG. 4, the assembly 10 includes the cylindrical coupler body or member 30, the eyebolt member 50, insert 70, and the set screw 80 that when assembled forms the single piece coupler assembly 10. In a preferred embodiment, the coupler body 30 is tubular in shape and has a longitudinal bore 32 surrounded by a wall 34. The bore 32 has a central axis C1 and a first or top portion 36 and a second or bottom portion 38. The top portion 36 is open-ended and includes internal threading 40. The second or bottom end portion 38 is closed. The coupler body 30 also has an upper portion 36A and a lower portion 38A. In a preferred embodiment, the upper portion 36A of the coupler body 30 has a larger diameter in relation to the lower portion 38A.

Figure 5A:
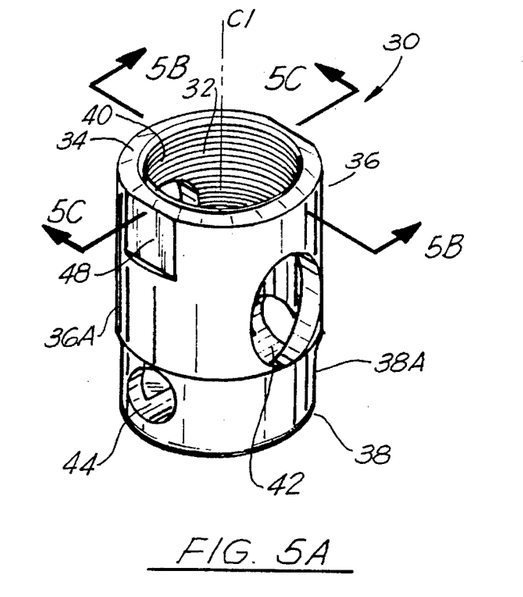
FIG. 5A is a side perspective view of the coupler member of the present invention.
Figure 5B:
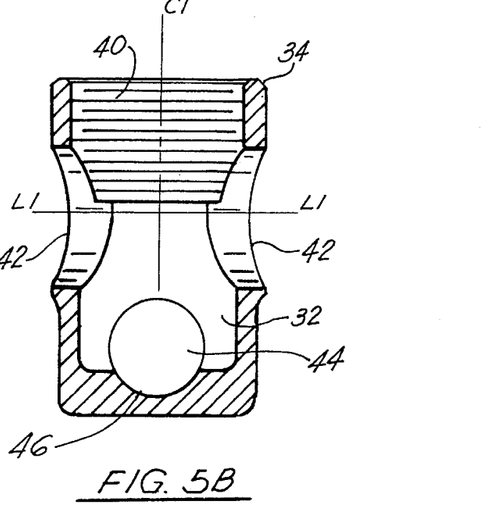
FIG. 5B is a cross-sectional view taken along sight line 5B—5B in FIG. 5A.
Figure 5C:
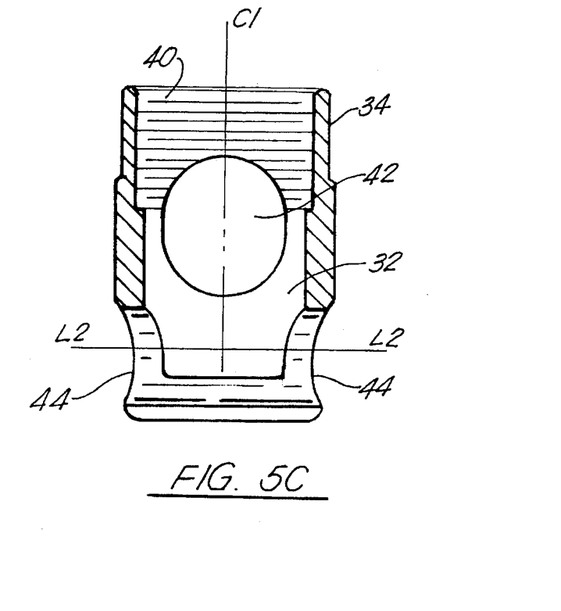
FIG. 5C is a cross-sectional view taken along sight line 5C—5C in FIG. 5A.

Coupler body 30 includes at least two through openings. In a preferred embodiment, coupler body 30 includes a first pair of openings through wall 34 aligned along a first line L1—L1 that intersects the central axis C1 of bore 32 at generally right angles (FIGS. 5A, 5B). Coupler body 30 also includes a second pair of openings 44 aligned along a second line L2—L2 that intersects the central axis C1 of bore 32 at generally right angles (FIGS. 5A, 5C). Openings 42 and 44 are generally perpendicular to each other and spaced apart from each other such that the periphery of the first pair of openings 42 is spaced longitudinally from the periphery of the second pair of openings 44 as shown in FIGS. 3, 4 and 5A. In a preferred embodiment, openings 42 are placed in the upper portion 36A of coupler body 30 and openings 44 are placed in the lower portion 38A of coupler body 30.

Openings 42 are sized and shaped to receive the spinal rod 12 with the longitudinal axis A1 of the rod 12 aligning with the line L1—L1 of the openings 42 when the rod 12 is placed through openings 42 of coupler body 30 (FIG. 3). Openings 44 have a lower wall portion 46 which is concave in shape in order to accommodate the cylindrical shank portion of the eyebolt 50 (FIG. 5B).

Figure 5D:
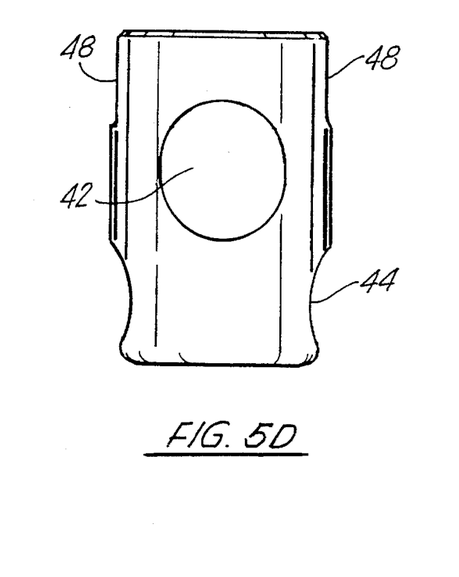
FIG. 5D is a side plan view of the coupler member of the present invention.

In a preferred embodiment, a pair of notches 48 are positioned on the outside surface of wall 34 at the open-ended portion 36 of coupler body 30 (FIGS. 5A, 5D). The notches 48 are sized and shaped to accommodate a tool such as a wrench which is used to stabilize the coupler body 30 while the set screw 80 is being tightened into place.

Figures 8A, 8B:
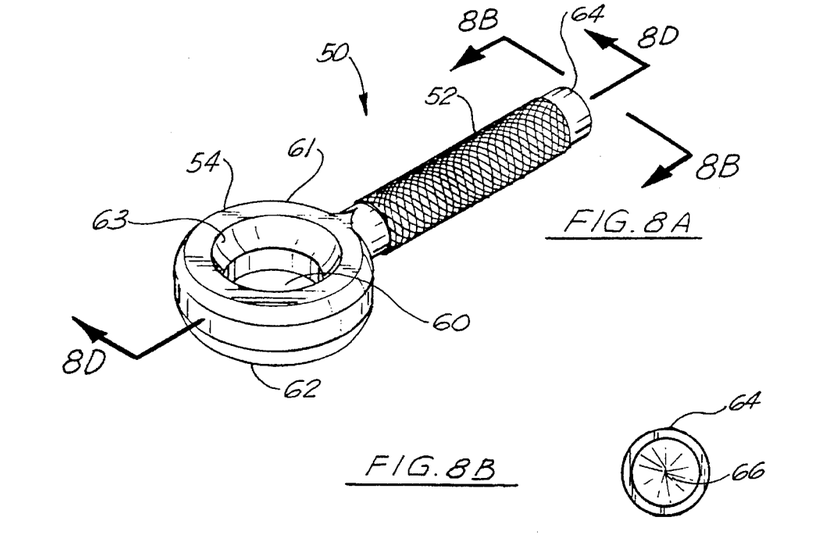
Figure 8C:
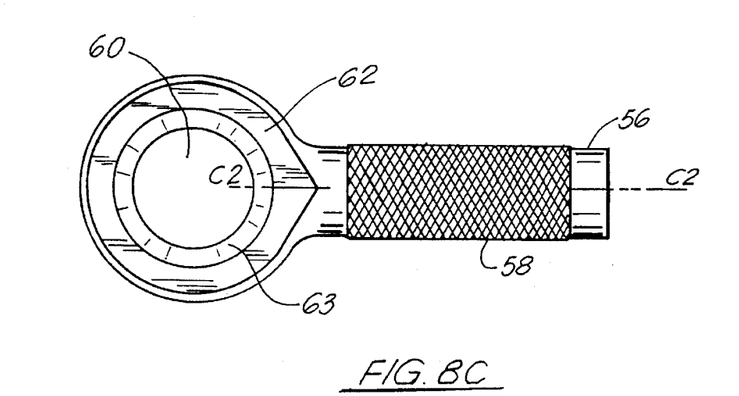
FIG. 8C is a lower plan view of the eyebolt of the present invention.
Figure 8D:
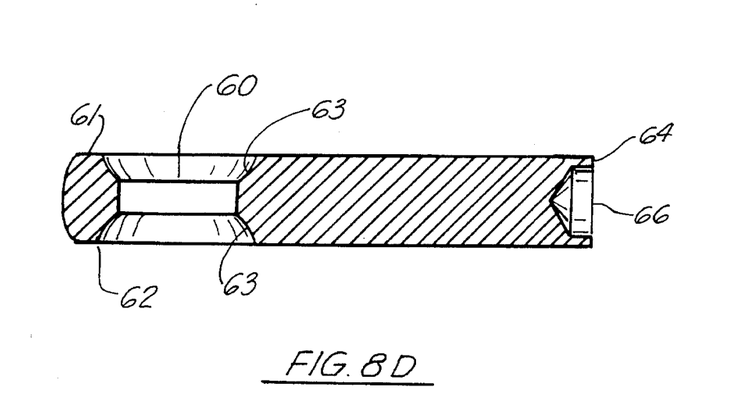
FIG. 8D is a cross-sectional view taken along sight line 8D—8D in FIG. 8A.

Eyebolt member 50 includes a shank portion 52 and an eye portion 54 (FIG. 8A). Shank portion 52 has a central axis C2—C2 and an outer surface 56 (FIG. 8C). In a preferred embodiment, shank portion 52 is cylindrical in shape with knurling 58 on a portion of the outer surface 56 (FIGS. 8A, 8C). Shank portion 52 includes a shank end 64 with a recess 66 so as to allow slight flanging of shank end 64 after the shank portion 52 is inserted through openings 44 of coupler body 30 (FIGS. 8B, 8D). The flanging prevents the shank portion 52 from sliding out of the openings 44 after the coupler assembly 10 has been assembled. When shank portion 52 of eyebolt 50 is inserted through openings 44 of coupler body 30, the shank portion's 52 central axis C2—C2 is aligned along line L2—L2 of openings 44 (FIG. 3).

Eye portion 54 of eyebolt 50 includes an opening 60, an upper surface 61, and a lower surface 62. Opening 60 has a spherically shaped surface 63 on the upper and lower surfaces 61, 62 of eye portion 54 and is sized and shaped to mate with the fastener 18. When implanted in a patient, the spherically shaped nut 28 mates with the spherically shaped surface 63 on the upper surface 61 of the eye portion opening 60 and the spherically shaped shoulder portion 24 mates with the spherically shaped surface 63 on the lower surface 62 of the eye portion opening 60. If the bone screw 18A is used as the bone fastener instead, the spherically shaped surface of the bone screw head portion 28A mates with the spherically shaped surface 63 on the upper surface 61 of the eye portion opening.

Figure 7A:
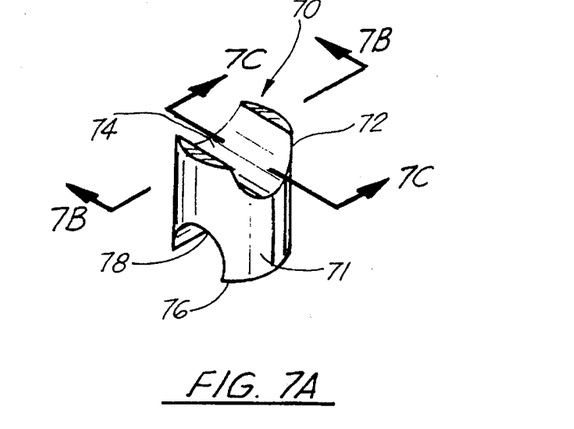
FIG. 7A is a side perspective view of the insert of the present invention.
Figure 7B:
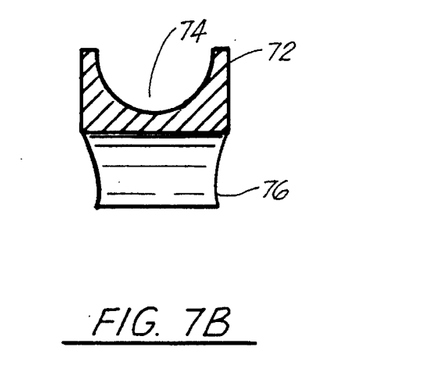
FIG. 7B is a cross-sectional view taken along sight line 7B—7B in FIG. 7A.
Figure 7C:
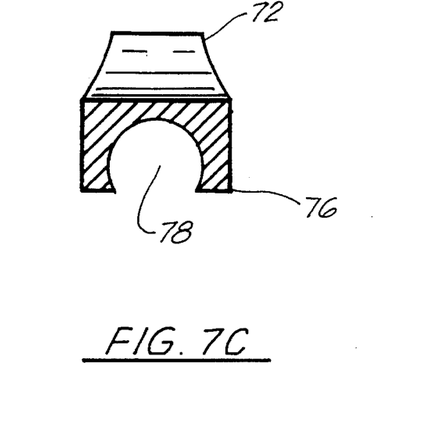
FIG. 7C is a cross-sectional view taken along sight line 7C—7C in FIG. 7A.

Insert 70 is cylindrical in shape and has opposed, arc-shaped end portions 72, 76 (FIG. 7A). First end portion 72 has a recess 74 that is sized and shaped to engage the spinal rod 12 (FIGS. 7A, 7B). Second end portion 76 has a recess 78 sized and shaped to engage the shank portion 52 of eyebolt 50 (FIGS. 7A, 7C). Insert 70 has an outer surface 71 that generally conforms to the shape of bore 32 of coupler body 30.

During assembly of the coupler assembly 10, insert 70 is placed in bore 32 after the shank portion 52 of eyebolt 50 has been placed through openings 44 of coupler body 30. Insert 70 is placed in bore 32 such that recess 78 contacts the outer surface 56 of shank portion 52 of eyebolt 50. When the spinal rod 12 is placed through the openings 42, recess 74 of insert 70 contacts the surface of the spinal rod 12. Thus, insert 70 provides greater surface to surface contact between the rod 12 and shank portion 72 then would be possible if the coupler assembly 10 was used without insert 70. In a coupler assembly 10 without insert 70, there would only be a single point of surface contact between the inserted rod 12 and shank portion 52 when they are in the perpendicular alignment allowed by the openings 42 and 44 of the coupler body 30.

Figure 6A:
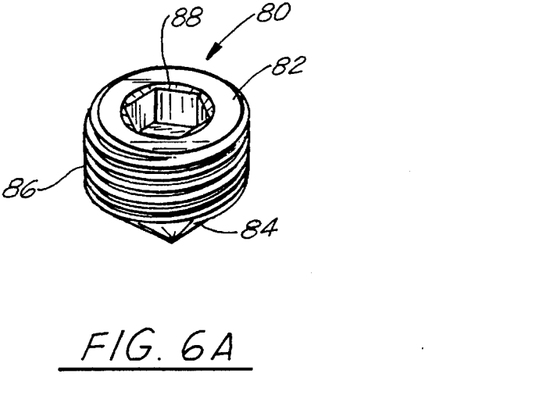
FIG. 6A is a side perspective view of the set screw of the apparatus of the present invention.
Figure 6B:
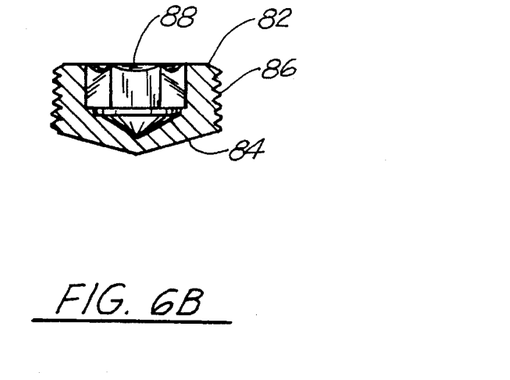
FIG. 6B is a cross-sectional view of the set screw in FIG. 6A.

Set screw 80 has an upper surface 82, a lower surface 84, and a threaded body portion 86 that engages and cooperates with the internally threaded end portion 36 of coupler body 30. Upper surface 82 is generally flat with a tool receptive socket 88 sized and shaped for receiving a tool designed to thread and tighten the set screw 80 into the threaded portion 40 of bore 32 of coupler body 30. In a preferred embodiment, lower surface 84 has a smooth outer surface and is generally conical in shape. The set screw 80 provides means for tightening the rod 12, insert 70, and eyebolt 50 within the coupler body 30.

In alternate embodiments, the coupler body can include a U-shaped top opening, sized and shaped to receive the spinal rod 12, instead of the pair of openings 42. A cap or a cross-bar with at least one set screw can be used to tighten the assembly 10 together instead of the set screw 80.

Coupler assembly 10 is assembled by placing shank portion 52 of eyebolt 50 through openings 44 of coupler body 30. Insert 70 is inserted in the bore 32 so as to allow recess 78 to engage the outer surface of shank portion 52. Set screw 80 is partially threaded into bore 32 which provides the single piece assembly 10 as shown in FIG. 3. After the fastener 18 has been implanted in pedicle 20 of vertebrae 16, the threaded end 26 of bone bolt 18 is inserted through the eyebolt opening 60 of coupler assembly 10. Spinal rod 12 is inserted through openings 42 such that the spinal rod 12 engages recess 74 of insert 70. After the coupler assembly 10 and rod 12 have been adjusted to conform to the anatomical structure of the vertebral column 14, set screw 80 is tightened into bore 32 of coupler body 30, securing the entire assembly 10A in place in the selected position.

The coupler assembly 10 allows for adjustment along four degrees of freedom, as shown in FIG. 3. Assembly 10 allows for movement along the longitudinal axis A1—A1 of spinal rod 12 which provides adjustment in a cephalad-caudad direction CC—CC. Eyebolt 50 can be moved in the openings 44 along the central axis C2 of shank portion 50 allowing for adjustment in a medial-lateral direction ML—ML. The rotation of the spinal rod 12 around its longitudinal axis A1—A1 in the openings 42 allows for angulation in a transverse plane TA—TA. The rotation of the eyebolt 50 around its central axis C2—C2 in openings 44 allows for angulation in a sagittal plane SA—SA.

Thus, the present invention provides a "single piece" connector for attaching a spinal rod to a vertebrae that facilitates rapid assembly and allows a wide range of adjustability in four axes of movement.

The coupler assembly 10 is formed of a biocompatible material, and in a preferred embodiment, is formed of stainless steel.

It should be understood that there can be improvements and modifications made to the embodiments of the invention described in detail above without departing from the spirit or scope of the invention, as set forth in the accompanying claims.

What is claimed is:

1. A spinal rod coupler assembly providing four degrees of freedom for connecting a spinal rod to a vertebrae of a patient, comprising:

a) a tubular coupler member having a longitudinal bore surrounded by a wall, the bore having a central axis and first and second end portions, the first end portion being open ended and internally threaded, the second end portion being closed;

b) a plurality of openings through the wall of the tubular coupler member, each of the openings communicating with the bore;

c) the plurality of openings including a first pair of openings aligning along a first line that intersects the central axis of the bore at generally right angles, and a second pair of openings aligning along a second line that intersects the central axis of the bore at generally right angles, the first and second lines being generally perpendicular to each other and spaced apart so that the periphery of the first pair of openings is spaced longitudinally from the periphery of the second pair of openings;

d) the first pair of openings sized and shaped for receiving a spinal rod having a longitudinal axis, which can be aligned with the first line of the first pair of openings of the coupler body;

e) an eyebolt having a shank portion with a central axis and an eye portion, the shank portion being insertable through the second pair of openings of the coupler body, aligning the central axis of the shank with the second line of the second pair of openings, the eye portion having an opening sized and shaped to mate with a selected fastener;

f) an insert that fits within the bore, the insert having an outer surface that generally conforms to the shape of the bore, the insert having opposed, arc-shaped end portions with recesses for engaging the spinal rod the eyebolt shank portion;

g) a set screw that threadably engages the internally threaded end portion of the bore so that the set screw tightens the assembly of the rod, insert, and eyebolt within the coupler member;

h) whereby the coupler assembly provides for movement along four degrees of freedom which include a movement along and a rotation about the longitudinal axis of the spinal rod, and a movement along and a rotation about the central axis of the eyebolt shank when the assembly is being implanted in a patient.

2. The coupler assembly of claim 1, wherein the eye portion of the eyebolt has an upper and a lower surface with the eye portion opening having a spherically shaped surface on the upper and lower surface of the eye portion.

3. The coupler assembly of claim 1, wherein the shank portion of the eyebolt has an outer surface with knurling on a portion of the outer surface.

4. The coupler assembly of claim 1, wherein the shank portion of the eyebolt includes a shank end with a recess so as to allow slight flanging of the shank end after the shank portion is inserted through the second pair of openings in the coupler body.

5. The coupler assembly of claim 1, wherein the tubular coupler member includes an upper portion and a lower portion with the first pair of openings positioned in the upper portion and the second pair of openings positioned in the lower portion.

6. The coupler assembly of claim 5, wherein the upper portion of the tubular coupler member has a larger diameter in relation to the lower portion of the tubular coupler member.

7. The coupler assembly of claim 1, wherein the set screw has an upper surface and a lower surface, the lower surface being generally conical in shape and the upper surface being generally flat with a tool receptive socket for receiving a tool designed to thread the set screw into the threaded portion of the bore.

8. A spinal prosthesis providing four degrees of freedom, comprising:

a) an elongated spinal rod having a central longitudinal axis;

b) a tubular coupler member having a longitudinal bore surrounded by a wall, the bore having a central axis and first and second end portions, the first end portion being open ended and internally threaded, the second end portion being closed;

c) a plurality of openings through the wall of the tubular coupler member, each of the openings communicating with the bore;

d) the plurality of openings including a first pair of openings aligning along a first line that intersects the central axis of the bore at generally right angles, and a second pair of openings aligning along a second line that intersects the central axis of the bore at generally right angles, the first and second lines being generally perpendicular to each other and spaced apart so that the periphery of the first pair of openings is spaced longitudinally from the periphery of the second pair of openings;

e) the first pair of openings sized and shaped to receive a spinal rod having a longitudinal axis with the rod being insertable through the first pair of openings, aligning the rod's longitudinal axis with the first line of the first pair of openings of the coupler body;

f) an eyebolt having a shank portion with a central axis and an eye portion, the shank portion being insertable through the second pair of openings of the coupler body, aligning the central axis of the shank with the second line of the second pair of openings, the eye portion having an opening sized and shaped to mate with a selected fastener;

g) an insert that fits within the bore, the insert having an outer surface that generally conforms to the shape of the bore, the insert having opposed, shaped end portions with recesses for engaging the spinal rod and the eyebolt shank portion;

h) a set screw that threadably engages the internally threaded end portion of the bore so that the set screw tightens the assembly of the rod, insert, and eyebolt within the coupler member;

i) the bone fastener for anchoring the coupler assembly to a patient's vertebrae, the bone bolt having a first threaded portion configured to be surgically implantable into a patient's bone tissue and a second portion having surfaces for engaging the eyebolt opening;

j) whereby the assembled spinal prosthesis provides for movement along four degrees of freedom which include a movement along and a rotation about the longitudinal axis of the spinal rod, and a movement along and a rotation about the central axis of the eyebolt shank when implanted in a patient.

9. The coupler assembly of claim 8, wherein the eyebolt has an upper and a lower surface with the eyebolt opening having a spherically shaped surface on the upper and lower surface of the eyebolt that cooperates with the surface of the bone fastener;

10. The coupler assembly of claim 8, wherein the shank portion of the eyebolt has an outer surface with knurling on a portion of the outer surface.

11. The coupler assembly of claim 8, wherein the shank portion of the eyebolt includes a shank end with a recess so as to allow slight flanging of the shank end after the shank portion is inserted through the second pair of openings in the coupler body.

12. The coupler assembly of claim 8, wherein the tubular coupler member includes an upper portion and a lower portion with the first pair of openings positioned in the upper portion and the second pair of openings positioned in the lower portion.

13. The coupler assembly of claim 12, wherein the upper portion of the tubular coupler member has a larger diameter in relation to the lower portion of the tubular coupler member.

14. The coupler assembly of claim 8, wherein the set screw has an upper surface and a lower surface, the lower surface being generally conical in shape and the upper surface being generally flat with a tool receptive socket for receiving a tool designed to thread the set screw into the threaded portion of the bore.

15. The coupler assembly of claim 8, wherein the bone fastener further includes a central non-threaded portion having a load transfer surface and an second threaded portion for threadably receiving a nut, the second threaded portion sized to be insertable through the eyebolt opening and able to be locked into place with the nut.

16. A spinal rod coupler assembly providing four degrees of freedom for connecting a spinal rod to a vertebrae of a patient, comprising:

a) a coupler member having a longitudinal bore surrounded by a wall, the bore having a central axis and first and second end portions, the first end portion being open ended and internally threaded, the second end portion being closed;

b) a plurality of openings in the coupler member, each of the openings communicating with the bore;

c) the plurality of openings including a first through opening aligning along a first line that intersects the central axis of the bore at generally right angles, and a second through opening aligning along a second line that intersects the central axis of the bore at generally right angles, the first and second lines being generally perpendicular to each other and spaced apart so that the periphery of the first opening is spaced longitudinally from the periphery of the second opening;

d) the first opening being sized and shaped to receive a spinal rod having a longitudinal axis, the rod's longitudinal axis aligning with the first line of the first opening of the coupler body;

e) an eyebolt member having a shank portion with a central axis and an eye portion, the shank portion being insertable through the second opening of the coupler body, aligning the central axis of the shank with the second line of the second opening, the eye portion having an opening sized and shaped to mate with a selected bone fastener;

f) means for tightening the assembly of the rod and eyebolt in a selected position within the coupler member;

g) whereby the coupler assembly provides for movement along four degrees of freedom which include a movement along and a rotation about the longitudinal axis of the spinal rod, and a movement along and a rotation about the central axis of the eyebolt shank when the assembly is being implanted in a patient.

* * * * *